(12) United States Patent
Okada et al.

(10) Patent No.: US 10,869,651 B2
(45) Date of Patent: Dec. 22, 2020

(54) ULTRASONIC PROBE AND ULTRASONIC DIAGNOSIS APPARATUS

(71) Applicant: Toshiba Medical Systems Corporation, Otawara (JP)

(72) Inventors: Kengo Okada, Kawasaki (JP); Hiroyuki Shikata, Nasushiobara (JP); Takahiro Sogou, Yokohama (JP)

(73) Assignee: Canon Medical Systems Corporation, Otawara (JP)

( * ) Notice: Subject to any disclaimer, the term of this patent is extended or adjusted under 35 U.S.C. 154(b) by 684 days.

(21) Appl. No.: 15/292,557

(22) Filed: Oct. 13, 2016

(65) Prior Publication Data

US 2017/0100095 A1 Apr. 13, 2017

(30) Foreign Application Priority Data

Oct. 13, 2015 (JP) .................................. 2015-202387
Oct. 12, 2016 (JP) .................................. 2016-201257

(51) Int. Cl.
| | |
|---|---|
| *A61B 8/14* | (2006.01) |
| *A61B 8/00* | (2006.01) |
| *A61B 1/005* | (2006.01) |
| *A61B 8/12* | (2006.01) |
| *A61B 1/00* | (2006.01) |

(52) U.S. Cl.
CPC .......... *A61B 8/445* (2013.01); *A61B 1/00006* (2013.01); *A61B 1/0055* (2013.01); *A61B 1/0057* (2013.01); *A61B 8/12* (2013.01); *A61B 8/56* (2013.01)

(58) Field of Classification Search
CPC combination set(s) only.
See application file for complete search history.

(56) References Cited

U.S. PATENT DOCUMENTS

| 8,376,950 | B2 | 2/2013 | Nagano et al. | |
|---|---|---|---|---|
| 2003/0028107 | A1* | 2/2003 | Miller | A61B 5/6819 600/437 |
| 2008/0300492 | A1* | 12/2008 | Nagano | A61B 8/12 600/462 |
| 2008/0312537 | A1* | 12/2008 | Hyuga | B06B 1/0622 600/459 |

FOREIGN PATENT DOCUMENTS

JP 2008-295749 A 12/2008

\* cited by examiner

*Primary Examiner* — Joel F Brutus
(74) *Attorney, Agent, or Firm* — Oblon, McClelland, Maier & Neustadt, L.L.P.

(57) ABSTRACT

An ultrasonic probe according to an embodiment includes a tip part, an operation part, a bending part, and a heat conducting part. The tip part includes transducer elements configured to transmit and receive ultrasound waves, electronic circuitry electrically connected to the transducer elements, and a frame having the electronic circuitry provided thereon. The operation part receives operations from an operator. The bending part includes a cable electrically connected to the electronic circuitry, and changes the orientation of the tip part by bending in accordance with operations performed on the operation part. The heat conducting part includes a unitary component extending from the tip part at least to the bending part, and is in contact with the frame in the tip part and in the close vicinity of the cable in the bending part.

19 Claims, 9 Drawing Sheets

ULTRASONIC PROBE AND ULTRASONIC DIAGNOSIS APPARATUS

CROSS-REFERENCE TO RELATED APPLICATIONS

This application is based upon and claims the benefit of priority from Japanese Patent Application No. 2015-202387, filed on Oct. 13, 2015; and Japanese Patent Application No. 2016-201257, filed on Oct. 12, 2016; the entire contents of which are incorporated herein by reference.

FIELD

An embodiment described herein relates generally to an ultrasonic probe and an ultrasonic diagnosis apparatus.

BACKGROUND

In present-day ultrasonic image diagnosis, an ultrasonic probe is used which enables observation of an organ surrounding a body cavity of a subject by being inserted into the body cavity. Such an ultrasonic probe is called an intracavitary probe. One type of intracavitary probe is a transesophageal echocardiography (TEE) probe. A transesophageal echocardiography probe is used, for example, in ultrasonic examination of the heart. One type of transesophageal echocardiography probe is a probe including two-dimensionally arranged transducer elements. Such an intracavitary probe is called a two-dimensional transesophageal echocardiography (2D-TEE) probe.

In a two-dimensional intracavitary probe, a group of transducer elements that transmit and receive ultrasound waves is arranged on electronic circuitry such as an application specific integrated circuit (ASIC) in some cases. This arrangement enables size reduction of a tip part in which the group of transducer elements and the electronic circuitry are housed. In addition, high-performance two-dimensional intracavitary probes have become available with the use of the electronic circuitry.

DETAILED DESCRIPTION

An ultrasonic probe according to an embodiment includes a tip part, an operation part, a bending part, and a heat conducting part. The tip part includes transducer elements configured to transmit and receive ultrasound waves, electronic circuitry electrically connected to the transducer elements, and a frame having the electronic circuitry provided thereon. The operation part receives operations from an operator. The bending part includes a cable electrically connected to the electronic circuitry, and changes the orientation of the tip part by bending in accordance with operations performed on the operation part. The heat conducting part includes a unitary component extending from the tip part at least to the bending part, and is in contact with the frame in the tip part and in the close vicinity of the cable in the bending part.

The following describes the ultrasonic probe and an ultrasonic diagnosis apparatus according to the embodiment with reference to the drawings. Embodiments are not limited to the embodiment described below.

Embodiment

Figure 1:
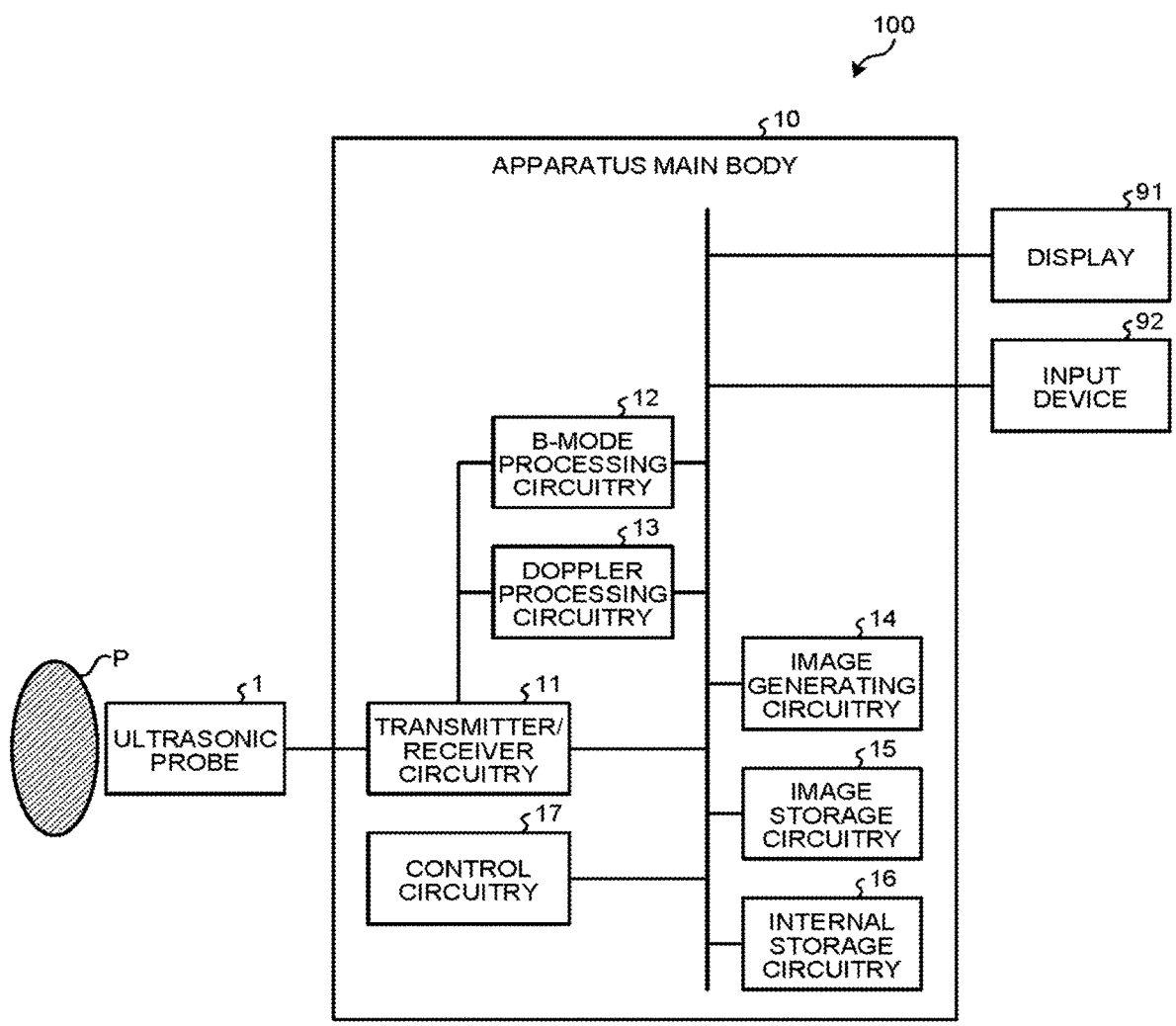
FIG. 1 is a diagram for explaining an example of the configuration of an ultrasonic diagnosis apparatus according to an embodiment.

First, the following describes an example of the configuration of an ultrasonic diagnosis apparatus including the ultrasonic probe according to the embodiment. FIG. 1 is a diagram for explaining an example of the configuration of an ultrasonic diagnosis apparatus 100 according to an embodiment. As illustrated in FIG. 1, the ultrasonic diagnosis apparatus 100 according to the embodiment includes an ultrasonic probe 1, a display 91, an input device 92, and an apparatus main body 10.

The ultrasonic probe 1 includes an ultrasonic transducer. The ultrasonic transducer includes a plurality of transducer elements that transmit ultrasonic waves and receive echoes (reflected waves). The transducer elements are two-dimensionally arranged. Each of the transducer elements generates an ultrasonic wave based on a drive signal supplied from electronic circuitry 22 described later. Each of the transducer elements receives an echo from a subject P, and converts the received echo into an echo signal, which is an electric signal. The ultrasonic transducer also includes components such as an acoustic matching layer provided to the transducer elements and a backside load member (backing material) that suppresses backward propagation of ultrasonic waves from the transducer elements. The ultrasonic probe 1 is detachably connected to the apparatus main body 10 via a connector 7 described later.

For example, when the ultrasonic waves are transmitted from the ultrasonic probe 1 to the subject P, the transmitted ultrasonic waves are successively reflected by a surface where acoustic impedance is discontinuous in body tissues of the subject P and turn into echoes, which are received by the transducer elements included in the ultrasonic probe 1. Each echo is converted into an echo signal by the transducer element that has received the echo. The amplitude of the echo signal depends on a difference in acoustic impedance across the discontinuous surface by which the corresponding ultrasonic wave is reflected. An echo signal generated when a transmitted ultrasonic pulse is reflected by a surface of a moving blood flow, a cardiac wall, or the like is subjected to a frequency shift due to the Doppler effect depending on a velocity component of a moving object with respect to an ultrasonic wave transmitting direction.

The display 91 displays a graphical user interface (GUI) through which an operator of the ultrasonic diagnosis apparatus 100 inputs various setting requests using the input device 92, and displays an ultrasonic image and other data generated in the apparatus main body 10. For example, the display 91 is implemented as a liquid crystal monitor, a cathode ray tube (CRT) monitor, a touch panel, or the like. The display 91 is connected to control circuitry 17 described later, and displays various pieces of information and data for various images, which are transmitted from the control circuitry 17, by converting those pieces of information and data into electric signals for display.

The input device 92 receives, from the operator, operations for inputting various instructions and various pieces of information. For example, the input device 92 is implemented as a component such as a trackball, a switch, a dial, a touch command screen, a foot switch, or a joystick. The input device 92 receives various setting requests from the operator of the ultrasonic diagnosis apparatus 100, and transfers the received various setting requests to the apparatus main body 10. For example, the input device 92 receives various setting requests for controlling the ultrasonic probe 1, and transfers the received various setting requests to the control circuitry 17.

The apparatus main body 10 is an apparatus that controls transmission and reception of ultrasonic waves by the ultrasonic probe 1, and generates an ultrasonic image based on echo signals corresponding to echoes received by the ultrasonic probe 1. The apparatus main body 10 includes, as illustrated in FIG. 1, transmitter/receiver circuitry 11, B-mode processing circuitry 12, Doppler processing circuitry 13, image generating circuitry 14, image storage circuitry 15, internal storage circuitry 16, and the control circuitry 17.

The transmitter/receiver circuitry 11 transmits, to the ultrasonic probe 1, a control signal for causing the electronic circuitry 22 described later to vibrate the transducer elements, in accordance with control from the control circuitry 17. Upon receiving echo data from the ultrasonic probe 1, the transmitter/receiver circuitry 11 transmits the received echo data to the B-mode processing circuitry 12 and the Doppler processing circuitry 13.

The B-mode processing circuitry 12 receives the echo data output from the transmitter/receiver circuitry 11, and performs, for example, logarithmic amplification and envelope detection processing on the received echo data to generate data (B-mode data) in which signal intensities are represented by brightness of luminance. The B-mode processing circuitry 12 is, for example, implemented as a processor.

The Doppler processing circuitry 13 receives the echo data output from the transmitter/receiver circuitry 11, performs frequency analysis on the from the received echo data to obtain velocity information therefrom, extracts echo components of a blood flow, tissue, and a contrast medium that are based on the Doppler effect, and generates data (Doppler data) obtained by extracting moving object information such as average velocities, dispersions, and power for multiple points. The Doppler processing circuitry 13 is, for example, implemented as a processor.

The image generating circuitry 14 generates an ultrasonic image from the data generated by the B-mode processing circuitry 12 and the Doppler processing circuitry 13. That is, the image generating circuitry 14 generates a B-mode image in which the intensities of echoes are represented by luminance from the B-mode data generated by the B-mode processing circuitry 12. The image generating circuitry 14 also generates, from the Doppler data generated by the Doppler processing circuitry 13, an average velocity image, a dispersion image, and a power image that represent the moving object information, or a color Doppler image as a combination thereof. That is, the image generating circuitry 14 generates the ultrasonic image based on the output from the ultrasonic probe 1.

The image storage circuitry 15 stores therein ultrasonic images generated by the image generating circuitry 14. The image storage circuitry 15 is capable of also storing therein the data generated by the B-mode processing circuitry 12 or the Doppler processing circuitry 13. For example, the image storage circuitry 15 is implemented as a semiconductor memory device such as a random access memory (RAM) or a flash memory, a hard disk, an optical disc, or the like.

The internal storage circuitry 16 stores therein: control programs for performing transmission and reception of ultrasonic waves, image processing, and display processing; and various kinds of data such as diagnostic information (such as, for example, patient identification data (ID) and findings of a doctor), diagnostic protocols, and various body marks. The internal storage circuitry 16 is used also, for example, for archiving data stored in the image storage circuitry 15 as needed. For example, the internal storage circuitry 16 is implemented as a semiconductor memory device such as a RAM or a flash memory, a hard disk, an optical disc, or the like.

The control circuitry 17 implements a function as an information processing apparatus (computer). The control circuitry 17 controls the entire processing in the ultrasonic diagnosis apparatus 100. For example, based on various setting requests input by the operator through the input device 92 and various control programs and various kinds of data read from the internal storage circuitry 16, the control circuitry 17 controls processing that the transmitter/receiver circuitry 11, the B-mode processing circuitry 12, the Doppler processing circuitry 13, and the image generating circuitry 14 perform. For example, the control circuitry 17 generates a control signal and controls the transmitter/receiver circuitry 11 so as to transmit the generated control signal to the ultrasonic probe 1. The control circuitry 17 also performs control to cause the display 91 to display thereon, for example, an ultrasonic image stored in the image storage circuitry 15, various images stored in the internal storage circuitry 16, a graphical user interface (GUI) for causing the image generating circuitry 14 to perform processing, and a processing result obtained by the image generating circuitry 14. The control circuitry 17 is, for example, implemented as a processor.

The term "processor" means, for example, circuitry such as a central processing unit (CPU), a graphics processing unit (GPU), an application specific integrated circuit (ASIC), or a programmable logic device (examples of which include a simple programmable logic device (SPLD), a complex programmable logic device (CPLD), and a field programmable gate array (FPGA)). Storing a computer program in the internal storage circuitry 16 may be replaced by a configuration in which the computer program is embedded directly in the circuitry of a processor. In this case, the processor implements a function by reading out and executing the computer program embedded in the circuitry.

The entire configuration of the ultrasonic diagnosis apparatus 100 according to the embodiment is described above.

Figure 2:
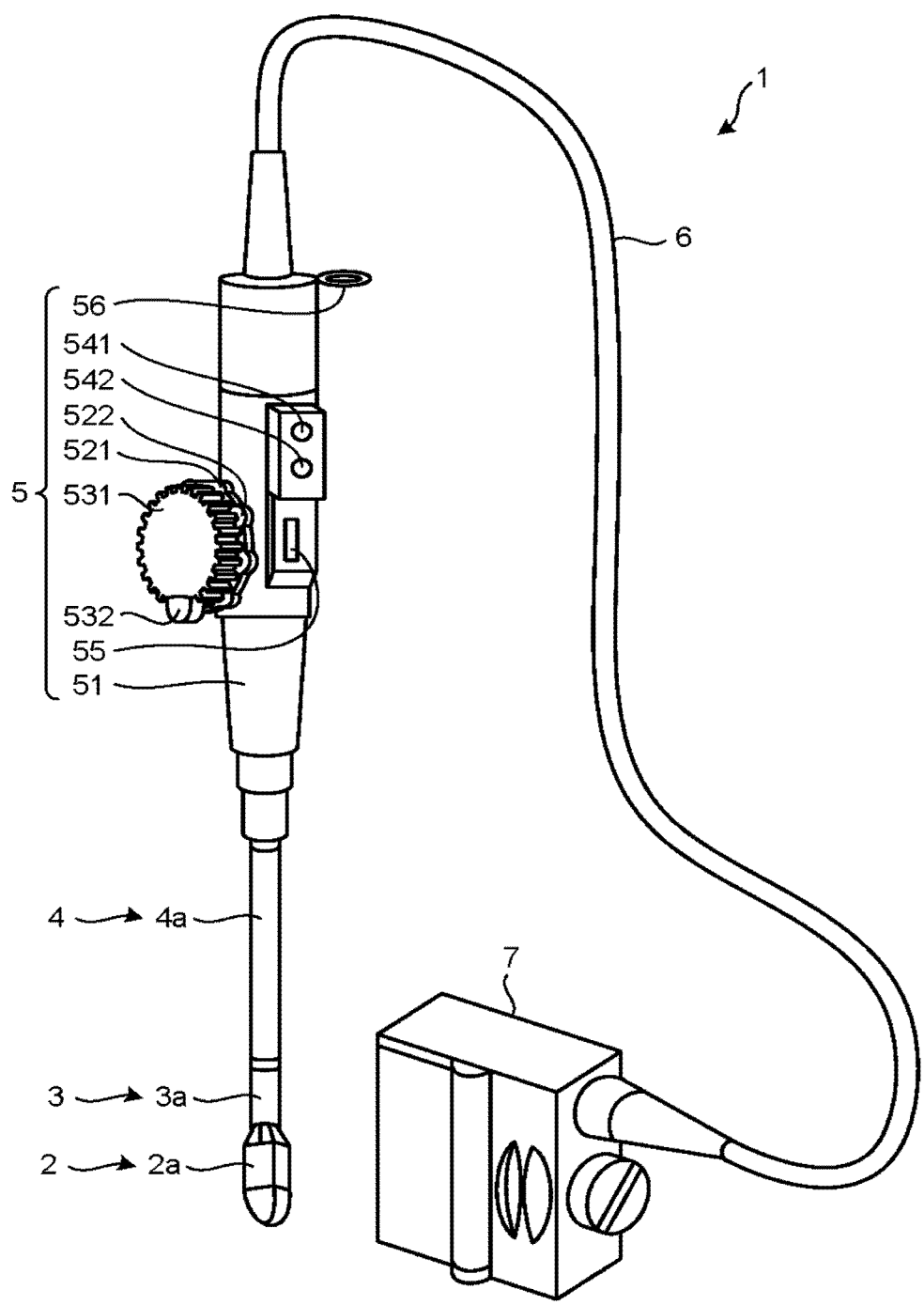
FIG. 2 is a view illustrating an example of the outer appearance of an ultrasonic probe according to the embodiment.

Next, the ultrasonic probe 1 according to the embodiment is described. FIG. 2 is a view illustrating an example of the outer appearance of the ultrasonic probe 1 according to the embodiment. Although the following describes a case where the ultrasonic probe 1 is a two-dimensional transesophageal echocardiography probe, the ultrasonic probe 1 is not limited to this case.

As illustrated in the example in FIG. 2, the ultrasonic probe 1 includes a tip part 2, a bending part 3, a guiding intermediate part 4, an operation part 5, a cable 6, and the connector 7.

The tip part 2 includes a tip armoring member 2a. The tip armoring member 2a is formed of, for example, biocompatible resin. The tip armoring member 2a houses components such as a frame 21 described later, the electronic circuitry 22 described later, and an ultrasonic transducer 24.

The bending part 3 includes an armoring member 3a. The armoring member 3a is a tubular member that houses components such as a bending mechanism 31 described later and a cable 8 described later. The armoring member 3a is bendable. The armoring member 3a is formed of, for example, rubber or resin that has flexibility. One end of the armoring member 3a is connected to the tip armoring member 2a. The other end of the armoring member 3a is connected to an armoring member 4a described later.

The guiding intermediate part 4 is inserted together with the tip part 2 and the bending part 3 into a body cavity of the subject P when an ultrasonic image of the subject P is captured. The guiding intermediate part 4 includes the armoring member 4a. The armoring member 4a is a tubular member that houses components such as a flexible tube 41 described later and the cable 8 described later. The armoring member 4a is connected to an armoring member 51 described later.

The operation part 5 receives operations from the operator. The operation part 5 includes the armoring member 51, a first knob 521, a first knob lock lever 522, a second knob 531, a second knob lock lever 532, a first rotation switch 541, a second rotation switch 542, a window 55, and a suspension ring 56.

The armoring member 51 is a tubular member to which components such as the first knob 521, the first knob lock lever 522, the second knob 531, the second knob lock lever 532, the first rotation switch 541, the second rotation switch 542, the window 55, and the suspension ring 56 are attached.

The first knob 521, the first knob lock lever 522, the second knob 531, and the second knob lock lever 532 are operated by the operator when the operator causes the bending mechanism 31 to bend. The first knob lock lever 522 is attached to the first knob 521. The second knob lock lever 532 is attached to the second knob 531. The first knob 521, the first knob lock lever 522, the second knob 531, and the second knob lock lever 532 are described later.

The first rotation switch 541 and the second rotation switch 542 are switches for rotating a captured ultrasonic image in diagnosis. The operator can observe the ultrasonic image from an angle appropriate for the diagnosis by operating the first rotation switch 541 and the second rotation switch 542.

The window 55 is a window for checking the bending state of the bending part 3. The suspension ring 56 is, as illustrated in FIG. 2, an annular member provided on the armoring member 51. The suspension ring 56 is used for suspending the ultrasonic probe 1 on a hook or the like provided on the apparatus main body 10 when ultrasonic images are not to be captured.

The cable 6 electrically connects the apparatus main body 10 to the cable 8 described later in the tip part 2. One end of the cable 6 is electrically connected to the connector 7; and the other end thereof is electrically connected to the cable 8 described later.

The connector 7 electrically connects the ultrasonic probe 1 to the apparatus main body 10 by being connected to the apparatus main body 10. To the connector 7, respective one-side ends of signal lines for transmitting signals communicated between the apparatus main body 10 and the tip part 2 are connected. The connector 7 includes terminals for electrically connecting these signal lines to the apparatus main body 10.

An example of the outer appearance of the ultrasonic probe 1 according to the embodiment is described above.

Here, while the ultrasonic probe 1 is transmitting and receiving ultrasonic waves, the transducer elements and the electronic circuitry 22 act as heat sources because of power consumption due to driving of the transducer elements in the ultrasonic transducer 24 and power consumption of the electronic circuitry 22. The tip part 2 thus produces heat. Because the tip part 2 is a part that makes contact with a patient P, the temperature of the tip part 2 needs to be controlled so as to fall within a safe range. Angle rings 31a in the bending part 3 described later are formed of alloy that poorly conducts heat such as stainless steel. Therefore, heat produced by the heat sources stagnates at the bending part 3, and has difficulty being conducted from the bending part 3 to the guiding intermediate part 4. In view of this inconvenience, the ultrasonic probe 1 according to this embodiment is configured to be able to suppress temperature increase of the tip part 2 during transmission and reception of ultrasonic waves.

Figure 3:
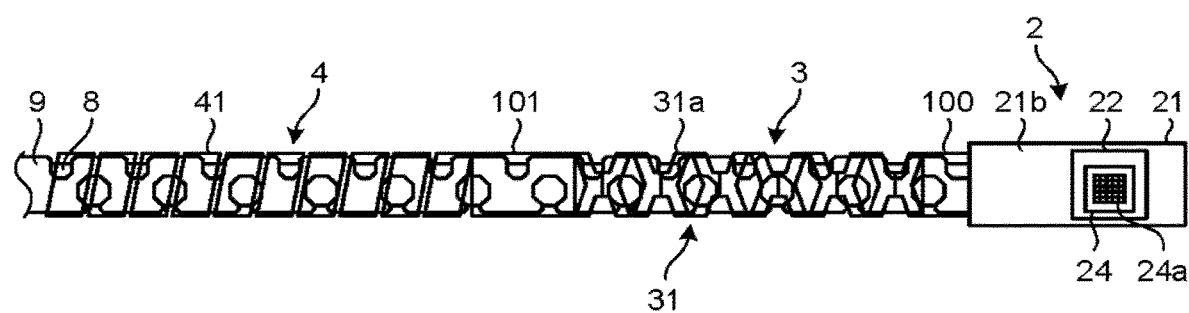
FIG. 3 is a view illustrating an example of the configuration of an ultrasonic probe according to the embodiment.

Next, an example of the configuration of the ultrasonic probe 1 according to the embodiment is described. FIG. 3 is a view illustrating an example of the structure of the ultrasonic probe 1 according to the embodiment. In the example in FIG. 3, the tip armoring member 2a, the armoring member 3a, and the armoring member 4a are not illustrated.

As illustrated in the example in FIG. 3, the tip part 2 of the ultrasonic probe 1 includes the frame 21, the electronic circuitry 22, and the ultrasonic transducer 24.

On the frame 21, components such as the electronic circuitry 22 and the ultrasonic transducer 24 are provided. The frame 21 is a member that holds components such as the electronic circuitry 22 and the ultrasonic transducer 24. The frame 21 is formed of a thermally conductive material. For example, metal is used as the thermally conductive material. In addition, the frame 21 has the function of serving as a skeleton for imparting rigidity to the tip part 2.

The ultrasonic transducer 24 includes a plurality of transducer elements 24a. The transducer elements 24a transmit and receive ultrasound waves. The transducer elements 24a are two-dimensionally arranged. Each of the transducer elements 24a generates ultrasonic waves based on a drive signal supplied from the electronic circuitry 22. Each of the transducer elements 24a receives an echo from the subject P and converts the received echo into an echo signal, which is an electric signal. The transducer element 24a then outputs the echo signal. Each of the transducer elements 24a thus produces heat when transmitting and receiving ultrasonic waves. The ultrasonic transducer 24 further includes components such as an acoustic matching layer provided to the transducer elements 24a and a backside load member that suppresses backward propagation of ultrasonic waves from the transducer elements 24a.

The electronic circuitry 22 is electrically connected to the transducer elements 24a and performs data processing on ultrasonic waves transmitted and received by the transducer elements 24a. The electronic circuitry 22 includes drive signal generating circuitry, delay circuitry, adder circuitry, and transmission/reception channel controlling circuitry.

The drive signal generating circuitry repeatedly generates, at a certain rate frequency (pulse repetition frequency (PRF)), a rate pulse for forming ultrasonic waves to be transmitted, and outputs the generated rate pulse as a drive signal for driving transducer elements 24a to the delay circuitry.

The delay circuitry has the function of executing certain delay processing on the drive signal output from the drive signal generating circuitry and supplying the drive signal subjected to the certain delay processing to each of the transducer elements 24a. In this embodiment, for example, one channel is assigned to each one of the transducer elements 24a, and the delay circuitry is provided with respect to each of the channels. For example, the delay circuitry executes delay processing of giving the drive signal supplied from the the drive signal generating circuitry a delay amount for a corresponding one of the transducer elements 24a needed for converging the ultrasonic waves generated from the transducer elements 24a into a beam and determining the transmission directivity thereof.

In addition to the function described above, the delay circuitry also has the function of, upon receiving an echo signal output from the transducer element 24a, executing delay processing for giving the received echo signal a delay amount needed for determining the reception directivity of the transducer elements 24a, and then outputting the echo signal subjected to the delay processing to the adder circuitry.

The adder circuitries are provided in such a manner that a group of transducer elements 24a that are included in a sub-array (group) corresponds to one of the adder circuitries. Each of the adder circuitries executes addition processing of adding up echo signals output from the delay circuitries corresponding to the transducer elements 24a included in the sub-array that corresponds to the adder circuitry. The adder circuitry then converts a resultant of the addition processing executed on the echo signals into digital data and performs phase-regulating addition processing on the digital data to generate echo data and output the generated echo data to the apparatus main body 10.

The transmission/reception channel controlling circuitry selects channels used for transmission and reception, and controls the corresponding ones of the above circuitries so that transmission and reception through the selected channels can be performed. It is not necessary that the electronic circuitry 22 include all of the kinds of circuitries described above, that is, the drive signal generating circuitry, the delay circuitry, the adder circuitry, and the transmission/reception channel controlling circuitry. One or some of those kinds of circuitry may be included in the transmitter/receiver circuitry 11 described above. For example, the electronic circuitry 22 needs only to include at least one kind of circuitry selected from among the drive signal generating circuitry, the delay circuitry, the adder circuitry, and the transmission/reception channel controlling circuitry.

Figure 4:
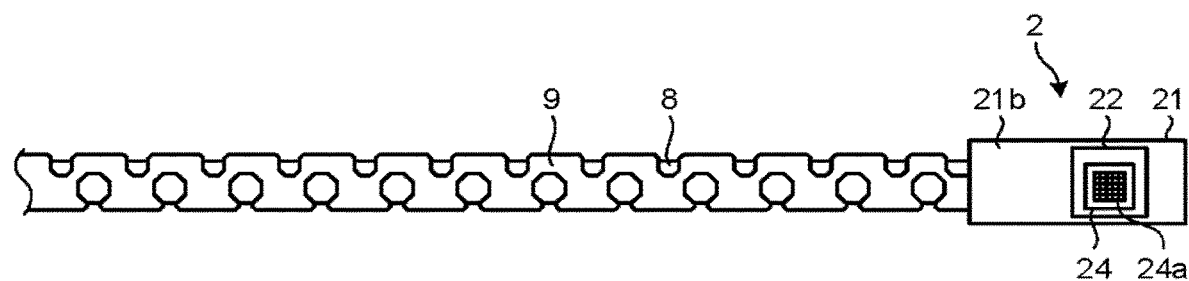
FIG. 4 is a view for explaining an example of a highly thermally conductive member according to the embodiment.

A highly thermally conductive member 9 constructed of one highly thermally conductive sheet-like member (thermally conductive sheet or thermally conductive component) is bonded to a surface of the frame 21 on the opposite side of a surface 21b. The highly thermally conductive member 9 may be composed of at least one highly thermally conductive member (thermally conductive sheet or thermally conductive member). The highly thermally conductive member 9 is an example of the heat conducting part. The following description assumes that the surface 21b of the frame 21, on which the electronic circuitry 22 and the ultrasonic transducer 24 are provided, is the "front surface" of the frame 21 and that the surface thereof on the opposite side of the front surface 21b is the "back surface" of the frame 21. That is, the electronic circuitry 22 and the transducer elements 24a of the ultrasonic transducer 24 are located on the front surface 21b side of the frame 21. Here, the highly thermally conductive member 9 bonded to the back surface of the frame 21 in the tip part 2 is described with reference to FIG. 4. FIG. 4 is a view for explaining an example of the highly thermally conductive member 9 according to the embodiment. The illustration of the example in FIG. 4 omits components such as members included in the bending part 3 and the guiding intermediate part 4.

As illustrated in FIG. 4, one end of the cable 8 is electrically connected to the tip part 2. More specifically, the one end of the cable 8 is electrically connected to flexible printed circuits (FPC) 30, which are described later, in the tip part 2. The other end of the cable 8 is electrically connected to the cable 6 described above.

The highly thermally conductive member 9 is a member for dissipating heat produced at the tip part 2.

The highly thermally conductive member 9 is overlaid on the cable 8 so as to cover the cable 8 and stuck. Consequently, the highly thermally conductive member 9 is brought into contact with the cable 8. However, it is not necessary that the highly thermally conductive member 9 make contact with the cable 8. For example, the highly thermally conductive member 9 may be provided around the cable 8 with another member interposed therebetween. That is, the highly thermally conductive member 9 needs only to be in the close vicinity of the cable 8.

In addition, while one end of the highly thermally conductive member 9 is bonded to the back surface of the frame 21 in the tip part 2 as described above, the other end thereof is stuck on the cable 8 in the guiding intermediate part 4 as illustrated in FIG. 3 to which reference has been already made. That is, the highly thermally conductive member 9 extends from the tip part 2 to the guiding intermediate part 4 in the example in FIG. 3 and FIG. 4. A direction in which the highly thermally conductive member 9 extends is the same as a direction in which the center axis of the cable 8 extends.

The other end of the highly thermally conductive member 9 may be stuck on the cable 8 in the bending part 3. That is, the highly thermally conductive member 9 may extend from the tip part 2 at least to the bending part 3. In this case also, it is not necessary that the highly thermally conductive member 9 make contact with the cable 8. For example, the highly thermally conductive member 9 needs only to be in the close vicinity of the cable 8.

The highly thermally conductive member 9 is constructed of a thermally conductive sheet that is a single member (a unitary component) obtained by, for example, laminating a plastic film on carbon graphite. That is, a thermally conductive sheet included as a unitary component in the highly thermally conductive member 9 is constructed of a member that contains carbon graphite. Carbon graphite is anisotropic in terms of thermal propagation, and has a difference in thermal propagation manner between the thickness direction and the plane direction thereof. For example, carbon graphite has thermal conductivity of at least 1 W/m·k in the thickness direction thereof and has thermal conductivity of at least 300 W/m·k in the plane direction thereof. The plane direction is, for example, a direction along a plane perpendicular to the thickness direction. As described so far, the highly thermally conductive member 9 has high thermal conductivity in the plane direction, and therefore is capable of efficiently transmitting, even to the guiding intermediate part 4 or the bending part 3 in the plane direction, heat produced at the tip part 2 when ultrasonic waves are transmitted and received. That is, the highly thermally conductive member 9 is capable of efficiently dissipating heat produced at the tip part 2. The ultrasonic probe 1 according to the embodiment is thus capable of suppressing temperature increase of the tip part 2 during transmission and reception of ultrasonic waves.

The highly thermally conductive member 9 may be constructed of, for example, a member that contains highly thermally conductive carbon nanotubes.

Based on the above description, the highly thermally conductive member 9 includes a unitary component (thermally conductive sheet) extending from the tip part 2 at least to the bending part 3, and is in contact with the frame 21 in the tip part 2 and in the close vicinity of the cable 8 in the bending part 3.

Furthermore, as illustrated in the example in FIG. 4, the highly thermally conductive member 9 has been machined into a mesh-like shape. By having a mesh-like shape, the highly thermally conductive member 9 is less likely to break because, even when the highly thermally conductive member 9 bends as a result of bending of the bending part 3, the highly thermally conductive member 9 bends in a manner following the bending part 3. Moreover, as illustrated in the example in FIG. 3, the highly thermally conductive member 9 is provided at a position inner than angle rings 31a described later. Therefore, when the bending part 3 bends, the curvature of the highly thermally conductive member 9 changes within a smaller range than in a case where the highly thermally conductive member 9 is provided at a position outer than the angle rings 31a described later. The curvature is the inverse of the radius of curvature of a member that has bent. When the curvature of the highly thermally conductive member 9 changes within a smaller range, the highly thermally conductive member 9 expands or contracts to a smaller extent. Therefore, accumulation of mechanical fatigue on the highly thermally conductive member 9 can be prevented. The ultrasonic probe 1 is thus capable of keeping the highly thermally conductive member 9 thermally conductive and bendable for long periods.

Here, an experiment was conducted in which, after the highly thermally conductive member 9 machined into a mesh-like shape was repeatedly bent several tens of thousands of times (for example, roughly ninety thousand times), the thermal conductivity thereof was measured. The result was that the thermal conductivity of the highly thermally conductive member 9 remained largely unchanged even after the highly thermally conductive member 9 were repeatedly bent several tens of thousands of times. This experiment result indicates that the ultrasonic probe 1 is capable of keeping the highly thermally conductive member 9 thermally conductive and bendable for long periods.

With reference back to FIG. 3, the bending part 3 includes the bending mechanism 31. The bending mechanism 31 changes the orientation of the tip part 2 by bending in accordance with operations performed on the operation part 5 illustrated in FIG. 2. The bending mechanism 31 includes a plurality of angle rings 31a. The angle rings 31a deform in accordance with operations performed on the operation part 5 illustrated in FIG. 2. Consequently, the bending mechanism 31 bends. Bending of the bending mechanism 31 causes a change in orientation of the tip part 2. That is, the bending part 3 changes the orientation of the tip part 2 by bending in accordance with operations performed on the operation part 5.

For example, the bending mechanism 31 includes a plurality of wires. One end of one of the wires is connected to the angle rings 31a, and the other end thereof is connected to a member interlocked with the first knob 521 illustrated in FIG. 2. In addition, one end of the other wire is connected to the angle rings 31a, and the other end thereof is connected to a member interlocked with the second knob 531 illustrated in FIG. 2.

The first knob 521 is operated by the operator when the operator causes the bending part 3 to bend within a certain plane. When the operator operates the first knob 521, the angle ring 31a connected to one of the wires that is connected to the member interlocked with the first knob 521 is pulled, so that this angle ring 31a deforms. The deformation of the angle ring 31a causes the bending mechanism 31 to bend within a certain plane, so that the orientation of the tip part 2 is changed within the certain plane.

The first knob lock lever 522 is operated by the operator when the operator fixes the orientation of the tip part 2 within the certain plane.

The second knob 531 is operated by the operator when the operator causes the bending part 3 to bend within a plane perpendicular to the certain plane. When the operator operates the second knob 531, the angle ring 31a connected to one of the wires that is connected to the member interlocked with the second knob 531 is pulled, so that this angle ring 31a deforms. The deformation of the angle ring 31a causes the bending mechanism 31 to bend within the place perpendicular to the certain plane, so that the orientation of the tip part 2 is changed within the plane perpendicular to the certain plane.

The second knob lock lever 532 is operated by the operator when the operator fixes the orientation of the tip part 2 within the plane perpendicular to the certain plane.

The ultrasonic probe 1 is thus capable of orienting, in accordance with operations performed on the first knob 521 and the second knob 531, the transducer elements 24a in a direction suitable for capturing ultrasonic images.

With reference back to FIG. 3, the guiding intermediate part 4 includes the flexible tube 41. The flexible tube 41 is overlaid on the highly thermally conductive member 9 and the cable 8 for protecting the highly thermally conductive member 9 and the cable 8.

Figure 5:
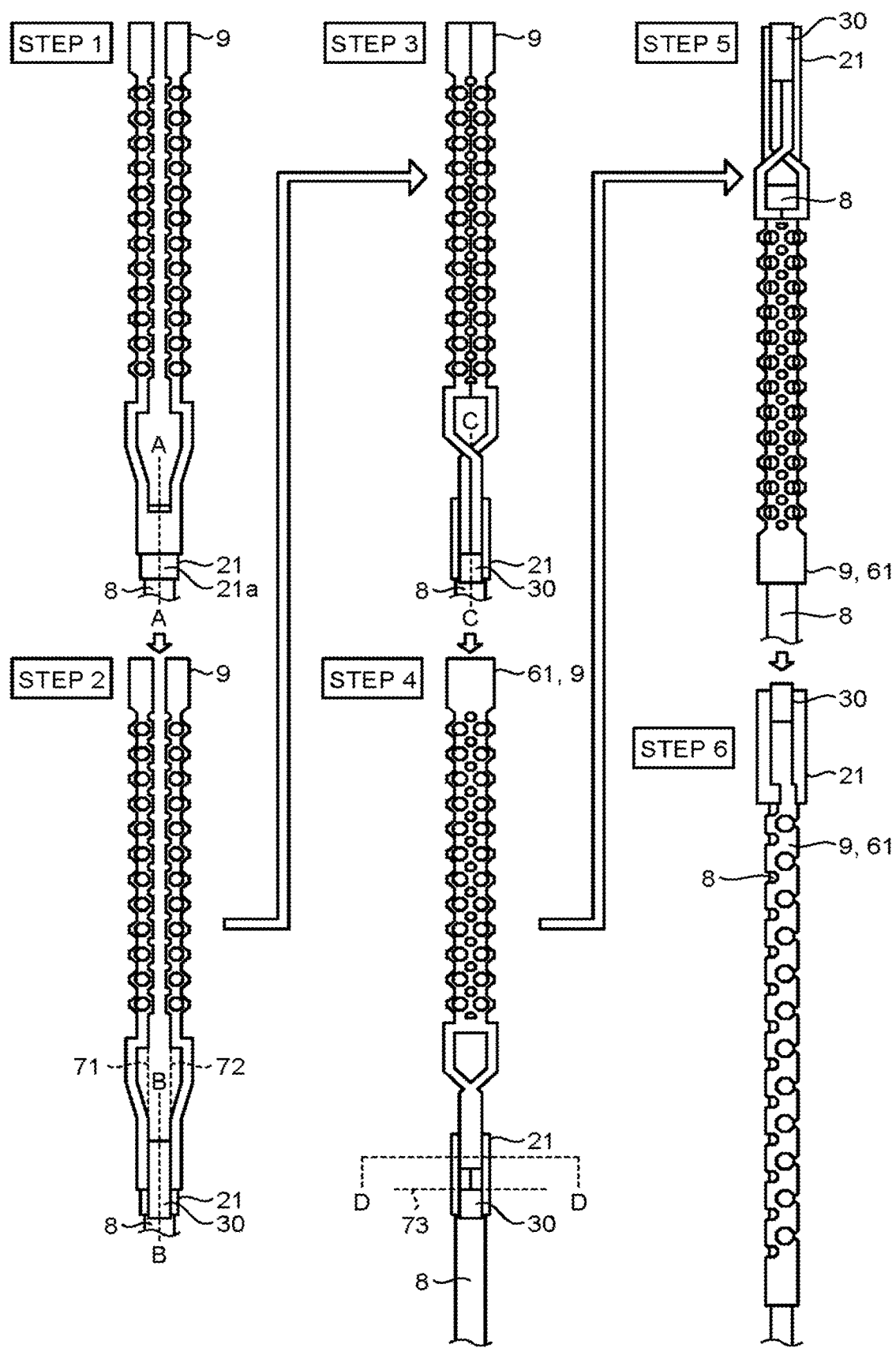
FIG. 5 is a view for explaining an example of how to attach the highly thermally conductive member.

Next, an example of how to attach the highly thermally conductive member 9 according to this embodiment is described. FIG. 5 is a view for explaining the example of how to attach the highly thermally conductive member 9. As illustrated in the example in FIG. 5, in the first place, the highly thermally conductive member 9 is joined to a back surface 21a of the frame 21 at Step 1. That is, the highly thermally conductive member 9 makes contact with the back surface 21a of the frame 21 in the tip part 2.

Figure 6:
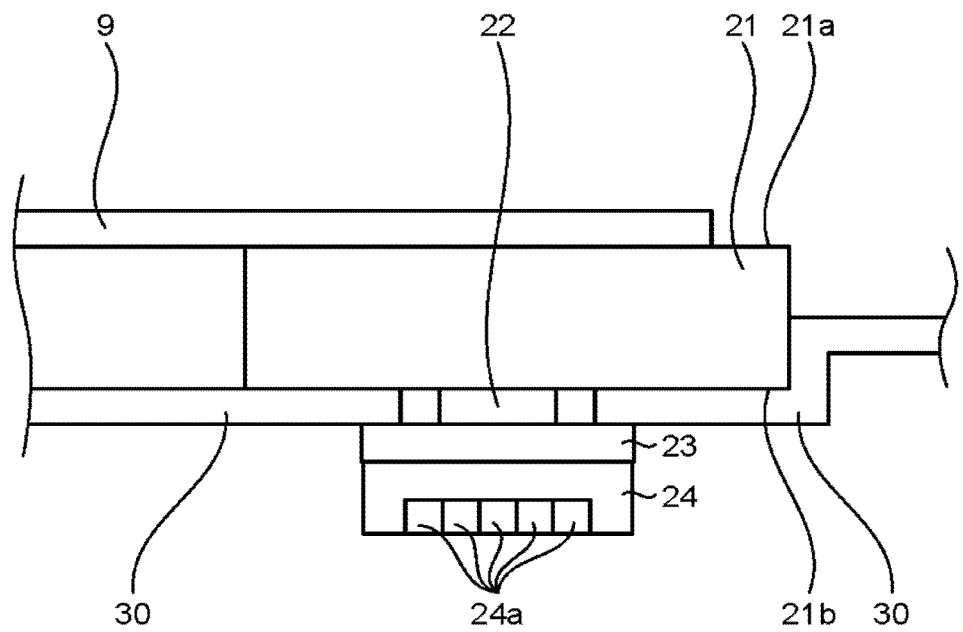
FIG. 6 is a sectional view taken along line A-A in FIG. 5.

FIG. 6 is a sectional view taken along line A-A in FIG. 5. As illustrated in FIG. 6, the highly thermally conductive member 9 is joined to the back surface 21a of the frame 21. To the front surface 21b of the frame 21, the electronic circuitry 22 is bonded with resin that has thermal conductivity. A rewiring layer 23 is provided on a surface on one side of the electronic circuitry 22 opposite to the side thereof on which the frame 21 is located. The electronic circuitry 22 is electrically connected to the FPC 30 through the rewiring layer 23.

The FPC 30 are an intermediary that electrically connects the electronic circuitry 22 and the cable 8 to each other. The FPC 30 are electrically connected to the cable 8. This cable 8 is electrically connected to the cable 6, so that the electronic circuitry 22 can receive control signals from the apparatus main body 10. The electronic circuitry 22 can also transmit the echo data to the apparatus main body 10. As illustrated in FIG. 6, the electronic circuitry 22 receives echo signals from the transducer elements 24a through the rewiring layer 23.

Figure 7:
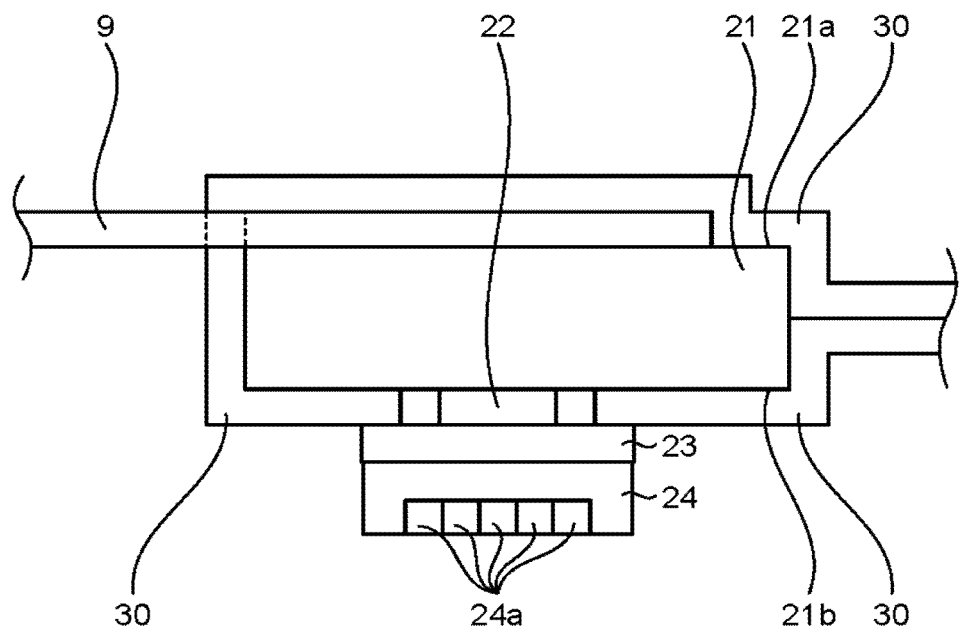
FIG. 7 is a sectional view taken along line B-B in FIG. 5.

As illustrated in the example in FIG. 5, at Step 2, the left one of the FPC 30 illustrated in FIG. 6 is folded so as to pass along the back surface 21a side of the frame 21. FIG. 7 is a sectional view taken along line B-B in FIG. 5. As illustrated in FIG. 7, the FPC 30 is folded so as to follow the shape of the frame 21 and pass along the back surface 21a side thereof.

Figure 8:
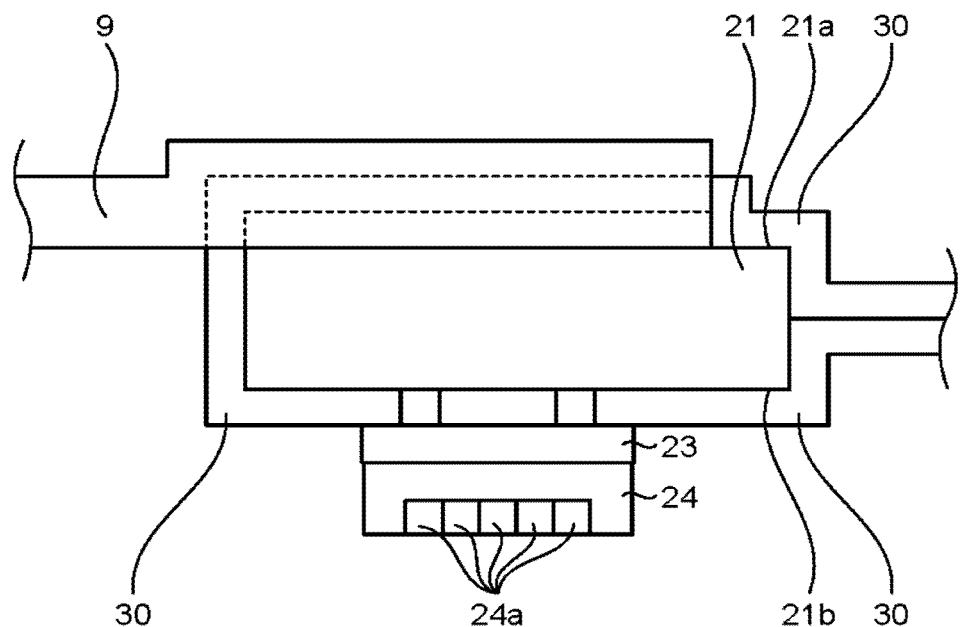
FIG. 8 is a sectional view taken along line C-C in FIG. 5.

As illustrated in the example in FIG. 5, at Step 3, the highly thermally conductive member 9 is folded inward along folding lines 71 and 72. FIG. 8 is a sectional view taken along line C-C in FIG. 5. As illustrated in FIG. 8, with the highly thermally conductive member 9 thus folded, the FPC 30 that passes along the back surface 21a side is interposed between the folded parts of the highly thermally conductive member 9. That is, the highly thermally conductive member 9 includes a folded sheet-like member (thermally conductive sheet).

Figure 9:
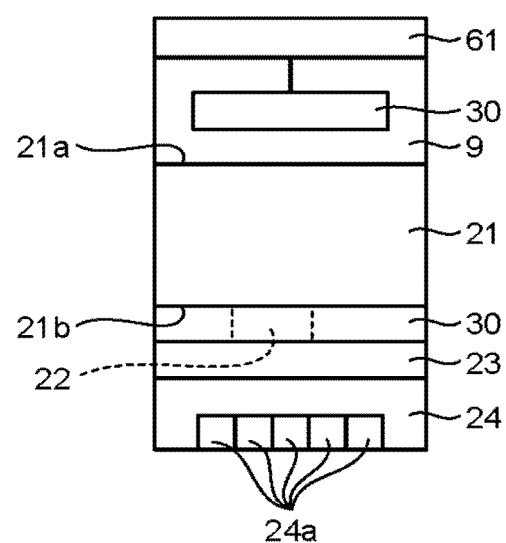
FIG. 9 is a sectional view taken along line D-D in FIG. 5.

As illustrated in the example in FIG. 5, at Step 4, a highly thermally conductive member 61 having a matching shape with the highly thermally conductive member 9 that have been folded at Step 3 is bonded to the highly thermally conductive member 9. FIG. 9 is a sectional view taken along line D-D in FIG. 5. As illustrated in FIG. 9, the transducer elements 24a and the electronic circuitry 22, which are members that produce heat, are provided on the front surface 21b of the frame 21, and the highly thermally conductive member 9 covering the perimeter of the FPC 30 is provided on the back surface 21a of the frame 21. In addition, the highly thermally conductive member 61 is bonded to the highly thermally conductive member 9.

Here, another configuration can be considered in which, while the FPC 30 is directly provided on the frame 21, the highly thermally conductive member 9 makes contact with the frame 21 with the FPC 30 interposed therebetween. However, this configuration makes it more difficult for heat to be conducted to the highly thermally conductive member 9 from the FPC 30 because the FPC 30 is poorly thermally conductive. Therefore, efficient dissipation of heat produced at the tip part 2 is impossible.

In contrast, the FPC 30 is not provided directly on the frame 21 in this embodiment, as illustrated in FIG. 9. In this embodiment, as illustrated in FIG. 9, once heat from the transducer elements 24a and the electronic circuitry 22 is transmitted through the frame 21 to the highly thermally conductive member 9, the heat is efficiently propagated in the plane direction of the highly thermally conductive member 9, so that the heat is efficiently transmitted to the highly thermally conductive member 61. As described so far, the FPC 30 are provided in such a manner that does not disturb thermal contact between the frame 21 and the highly thermally conductive member 9.

Furthermore, in this embodiment, the highly thermally conductive member 61 is bonded to the highly thermally conductive member 9. The sectional area of the aggregate of the highly thermally conductive members is therefore large. A highly thermally conductive member having a larger sectional area propagates a lager total amount of heat. In this embodiment, efficient heat dissipation is enabled because the total amount of propagated heat is thus large. Although the configuration having the two highly thermally conductive members 9 and 31 bonded to each other is described above, three or more highly thermally conductive members may be bonded to one another, or only one highly thermally conductive member may be included.

As illustrated in the example in FIG. 5, at Step 5, the highly thermally conductive member 9 having the highly thermally conductive member 61 bonded thereto is folded back from the tip part 2 side to the cable 8 side along a folding line 73. Subsequently, at Step 6, the highly thermally conductive member 9 having the highly thermally conductive member 61 bonded thereto is wrapped around the cable 8. Consequently, for example, the highly thermally conductive member 9 is wrapped around the cable 8 in the bending part 3.

Figure 10:
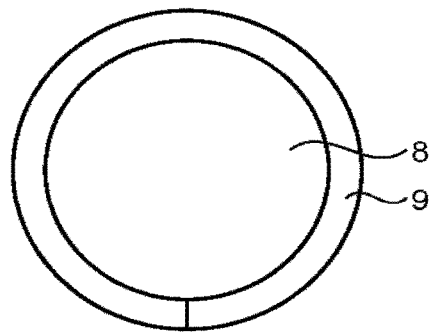
FIG. 10 is a sectional view of a cable having the highly thermally conductive member wrapped around the cable at Step 6.

FIG. 10 is a sectional view of the cable 8 having the highly thermally conductive member 9 wrapped around the cable 8 at Step 6. As illustrated in the example in FIG. 10, in this embodiment, the width of the highly thermally conductive member 9 is at least the circumferential length of the cable 8, so that the highly thermally conductive member 9 entirely covers the circumference of the cable 8. That is, the highly thermally conductive member 9 has a large heat-dissipating area, thereby being capable of efficiently diffusing heat from the heat sources.

The ultrasonic probe 1 and the ultrasonic diagnosis apparatus 100 according to the embodiment are as described above. The ultrasonic probe 1 and the ultrasonic diagnosis apparatus 100 according to the embodiment are capable of suppressing temperature increase of the tip part 2 during transmission and reception of ultrasonic waves.

First Modification According to the Embodiment

Here, the above embodiment describes a case in which the width of the highly thermally conductive member 9 is at least the circumferential length of the cable 8. However, the width of the highly thermally conductive member 9 may be smaller than the circumferential length of the cable 8. Such an embodiment is described here as a first modification according to the embodiment.

Figure 11:
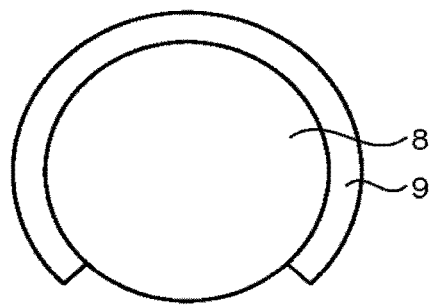
FIG. 11 is a sectional view of a cable having a highly thermally conductive member according to a first modification wrapped around the cable.

FIG. 11 is a sectional view of the cable 8 having the highly thermally conductive member 9 according to the first modification wrapped around the cable 8. As illustrated in the example in FIG. 11, the width of the highly thermally conductive member 9 is smaller than the circumferential length of the cable 8. Therefore, the highly thermally conductive member 9 partially covers the circumference of the cable 8. In the first modification, a highly thermally conductive member of a smaller size is used as the highly thermally conductive member 9. The use of the highly thermally conductive member 9 of a smaller size makes it possible to hold down the costs, such as a price, thereof. Thus, according to the first modification, the highly thermally conductive member 9 of a smaller size is used, so that temperature increase of the tip part 2 can be suppressed with costs held down.

Second Modification According to the Embodiment

The above embodiment also describes a case in which the highly thermally conductive member 9 has a mesh-like shape. However, the shape of the highly thermally conductive member 9 is not limited to this case. Here, other shapes of the highly thermally conductive member 9 are described as a second modification and a third modification according to the embodiment.

Figure 12:
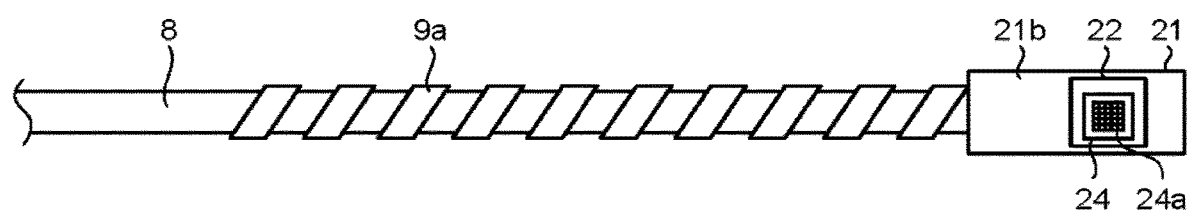
FIG. 12 is a view for explaining an example of a highly thermally conductive member according to a second modification.

First, the second modification is described. FIG. 12 is a view for explaining an example of a highly thermally conductive member according to the second modification. As illustrated in the example in FIG. 12, a highly thermally conductive member 9a according to the second modification has a narrow ribbon-like shape. The highly thermally conductive member 9a has a heat-dissipating area sufficiently large for diffusing heat produced at the tip part 2. The highly thermally conductive member 9a is spirally wrapped around the cable 8 with a certain pitch between each neighboring turns, as illustrated in the example in FIG. 12. For example, the highly thermally conductive member 9a is spirally wrapped around the cable 8 in the bending part 3. In the same manner as in the above-described embodiment, one end of the highly thermally conductive member 9a is connected to the back surface 21a of the frame 21, and the other end thereof is connected to the cable 8 in the bending part 3 or the guiding intermediate part 4. By having the highly thermally conductive member 9a wrapped around the cable 8, the highly thermally conductive member 9a is less likely to break because, even when the highly thermally conductive member 9a bends as a result of bending of the bending part 3, the highly thermally conductive member 9a bends in a manner following the bending part 3. The ultrasonic probe according to the second modification is thus capable of keeping the highly thermally conductive member 9a thermal conductive and bendable for long periods.

In addition, in the same manner as in the above-described embodiment, temperature increase of the tip part 2 during transmission and reception of ultrasonic waves can be suppressed also in the second modification.

Third Modification According to the Embodiment

Figure 13:
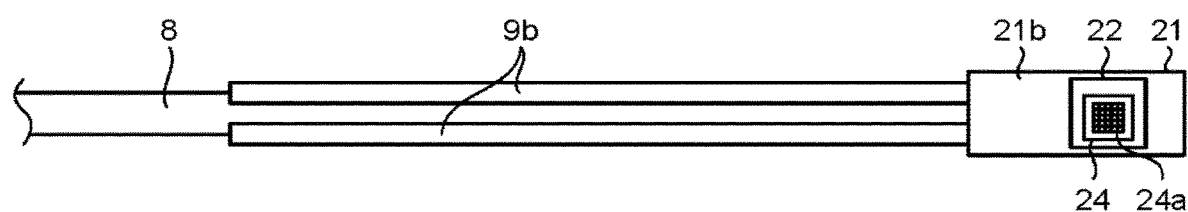
FIG. 13 is a view for explaining an example of a highly thermally conductive member according to a third modification.

Next, the third modification is described. FIG. 13 is a view for explaining an example of a highly thermally conductive member according to a third modification. As illustrated in the example in FIG. 13, the highly thermally conductive member according to the third modification is divided, along a direction in which it extends, into a plurality of highly thermally conductive members 9b. The highly thermally conductive members 9b have a heat-dissipating area sufficiently large for diffusing heat produced at the tip part 2. In the same manner as in the above-described embodiment, ends of the highly thermally conductive members 9b on one side are connected to the back surface 21a of the frame 21, and the other ends thereof are connected to the cable 8 in the bending part 3 or the guiding intermediate part 4. The division into the highly thermally conductive members 9b makes the highly thermally conductive members 9b less likely to break because, even when the highly thermally conductive members 9b bend as a result of bending of the bending part 3, the highly thermally conductive members 9b bend in a manner following the bending part 3. The ultrasonic probe according to the third modification is thus capable of keeping the highly thermally conductive members 9b thermally conductive and bendable for long periods.

In addition, in the same manner as in the above-described embodiment, temperature increase of the tip part 2 during transmission and reception of ultrasonic waves can be suppressed also in the third modification.

Fourth Modification According to the Embodiment

Still other shapes of the highly thermally conductive member 9 are described as a fourth modification and a fifth modification according to the embodiment.

Figure 14:
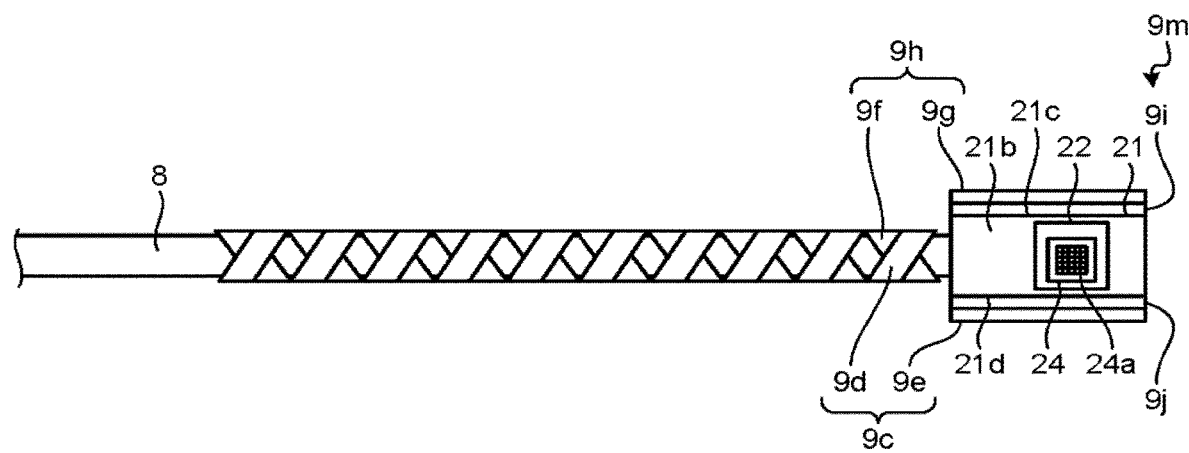
FIG. 14 is a view for explaining an example of a highly thermally conductive member according to a fourth modification.

FIG. 14 is a view for explaining an example of a highly thermally conductive member according to the fourth modification. As illustrated in the example in FIG. 14, a first highly thermally conductive member 9d of a highly thermally conductive member 9c and a third highly thermally conductive member 9f of a highly thermally conductive member 9h according to the fourth modification are spirally wrapped around the cable 8 in the bending part 3 in such a manner as to cross each other. As illustrated in the example in FIG. 14, the first highly thermally conductive member 9d and the third highly thermally conductive member 9f spirally cross each other.

The first highly thermally conductive member 9d and the third highly thermally conductive member 9f have heat-dissipating areas sufficiently large for diffusing heat produced at the tip part 2. In the same manner as in the above-described embodiment, ends of the first highly thermally conductive member 9d and the third highly thermally conductive member 9f on one side are connected to the cable 8 in the bending part 3 or the guiding intermediate part 4. By being wrapped around the cable 8, the first highly thermally conductive member 9d and the third highly thermally conductive member 9f are less likely to break because, even when the first highly thermally conductive member 9d and the third highly thermally conductive member 9f bend as a result of bending of the bending part 3, the first highly thermally conductive member 9d and the third highly thermally conductive member 9f bend in a manner following the bending part 3. The ultrasonic probe according to the fourth modification is thus capable of keeping the first highly thermally conductive member 9d and the third highly thermally conductive member 9f thermally conductive and bendable for long periods.

In addition, in the same manner as in the above described embodiment, temperature increase of the tip part 2 during transmission and reception of ultrasonic waves can be suppressed also in the fourth modification.

Figure 15:
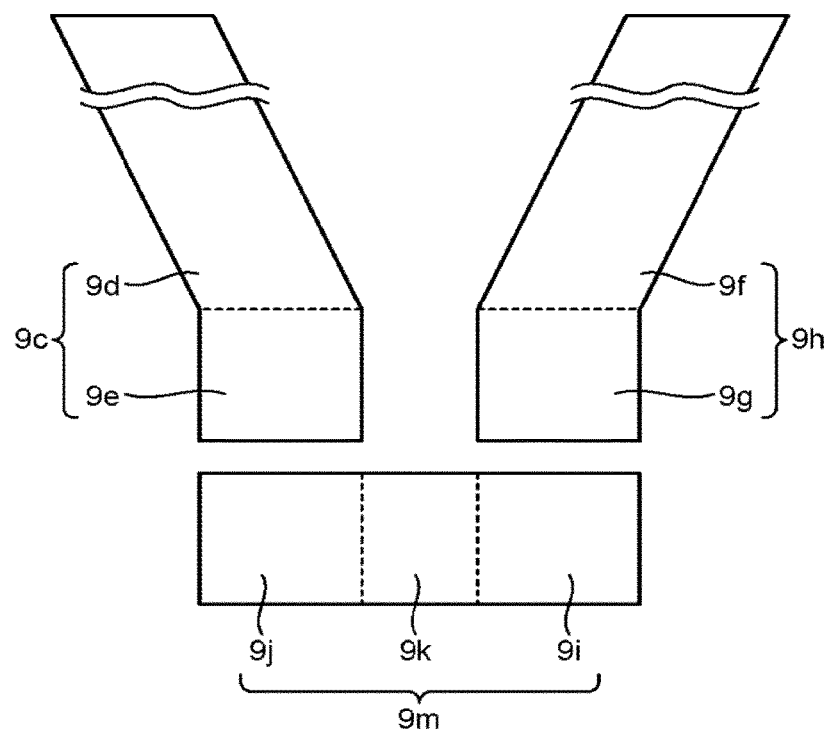
FIG. 15 is a view for explaining an example of how to attach the highly thermally conductive member according to the fourth modification.

Here, with reference to FIG. 15, an example of how to attach the highly thermally conductive member according to the fourth modification is described. FIG. 15 is a view for explaining the example of how to attach the highly thermally conductive member according to the fourth modification.

As illustrated in FIG. 15, the highly thermally conductive member according to the fourth modification is separated into three highly thermally conductive members 9c, 9h, and 9m.

The highly thermally conductive member 9c includes the first highly thermally conductive member 9d and a second highly thermally conductive member 9e. The first highly thermally conductive member 9d and the second highly thermally conductive member 9e are integrally molded. The first highly thermally conductive member 9d has a substantially parallelogram-like shape when viewed from the top. The second highly thermally conductive member 9e is rectangular when viewed from the top.

The highly thermally conductive member 9h includes the third highly thermally conductive member 9f and a fourth highly thermally conductive member 9g. The third highly thermally conductive member 9f and the fourth highly thermally conductive member 9g are integrally molded. The third highly thermally conductive member 9f has a substantially parallelogram-like shape when viewed from the top. The fourth highly thermally conductive member 9g is rectangular when viewed from the top.

The highly thermally conductive member 9c and the highly thermally conductive member 9h are different when viewed from the top.

The highly thermally conductive member 9m includes a fifth highly thermally conductive member 9i, a sixth highly thermally conductive member 9j, and a seventh highly thermally conductive member 9k. The fifth highly thermally conductive member 9i, the sixth highly thermally conductive member 9j, and the seventh highly thermally conductive member 9k are integrally molded.

Here, the example of how to attach the highly thermally conductive member according to the fourth modification is described. First, as illustrated in FIG. 14, the fifth highly thermally conductive member 9i of the highly thermally conductive member 9m is joined to a side surface 21c of the frame 21, and the sixth highly thermally conductive member 9j of the highly thermally conductive member 9m is joined to a side surface 21d of the frame 21. In addition, the seventh highly thermally conductive member 9k of the highly thermally conductive member 9m is joined to the back surface 21a of the frame 21.

Subsequently, as illustrated in FIG. 14, the fourth highly thermally conductive member 9g of the highly thermally conductive member 9h is stuck on the fifth highly thermally conductive member 9i. Subsequently, as illustrated in FIG. 14, the third highly thermally conductive member 9f of the highly thermally conductive member 9h is spirally wrapped around the cable 8.

Subsequently, as illustrated in FIG. 14, the second highly thermally conductive member 9e of the highly thermally conductive member 9c is stuck on the sixth highly thermally conductive member 9j. Subsequently, as illustrated in FIG. 14, the first highly thermally conductive member 9d of the highly thermally conductive member 9c is spirally wrapped around the cable 8 in such a manner as to cross the third highly thermally conductive member 9f.

In this manner, the highly thermally conductive members spirally crossing each other are wrapped around the cable 8 in the fourth modification.

Fifth Modification According to the Embodiment

Figure 16:
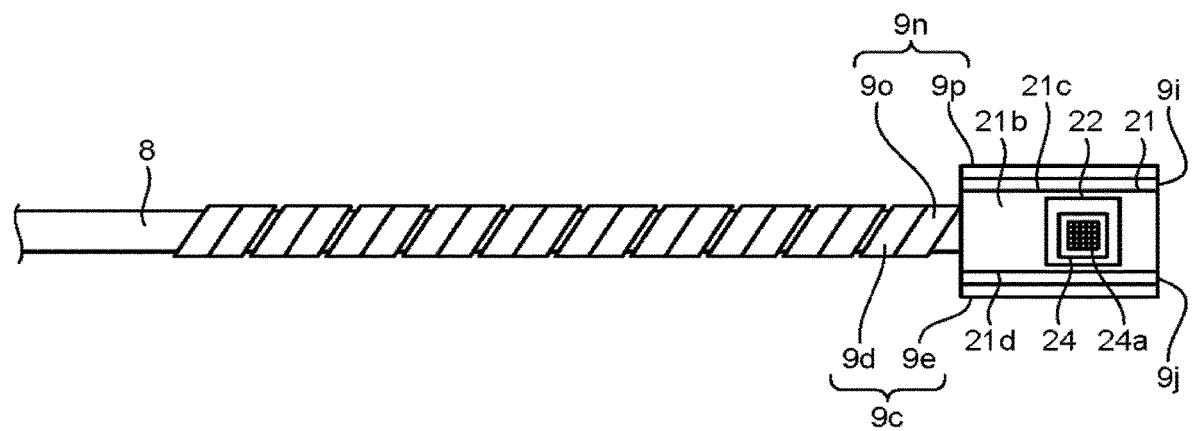
FIG. 16 is a view for explaining an example of a highly thermally conductive member according to a fifth modification.

Next, an example of a highly thermally conductive member according to the fifth modification is described. FIG. 16 is a view for explaining an example of the highly thermally conductive member according to the fifth modification. As illustrated in the example in FIG. 16, the first highly thermally conductive member 9d of the highly thermally conductive member 9c and an eighth highly thermally conductive member 9o of a highly thermally conductive member 9n according to the fifth modification are wrapped around the cable 8 spirally in the same direction in the bending part 3. As illustrated in the example in FIG. 16, the first highly thermally conductive member 9d and the eighth highly thermally conductive member 9o form a double-stranded spiral. The first highly thermally conductive member 9d and the eighth highly thermally conductive member 9o may overlap each other.

The first highly thermally conductive member 9d and the eighth highly thermally conductive member 9o have heat-dissipating areas sufficiently large for diffusing heat produced at the tip part 2. In the same manner as in the above-described embodiment, ends of The first highly thermally conductive member 9d and the eighth highly thermally conductive member 9o on one side are connected to the cable 8 in the bending part 3 or the guiding intermediate part 4. By being wrapped around the cable 8, the first highly thermally conductive member 9d and the eighth highly thermally conductive member 9o are less likely to break because, even when the first highly thermally conductive member 9d and the eighth highly thermally conductive member 9o bend as a result of bending of the bending part 3, the first highly thermally conductive member 9d and the eighth highly thermally conductive member 9o bend in a manner following the bending part 3. The ultrasonic probe according to the fifth modification is thus capable of keeping the first highly thermally conductive member 9d and the eighth highly thermally conductive member 9o thermally conductive and bendable for long periods.

In addition, in the same manner as in the above-described embodiment, temperature increase of the tip part 2 during transmission and reception of ultrasonic waves can be suppressed also in the second modification.

Figure 17:
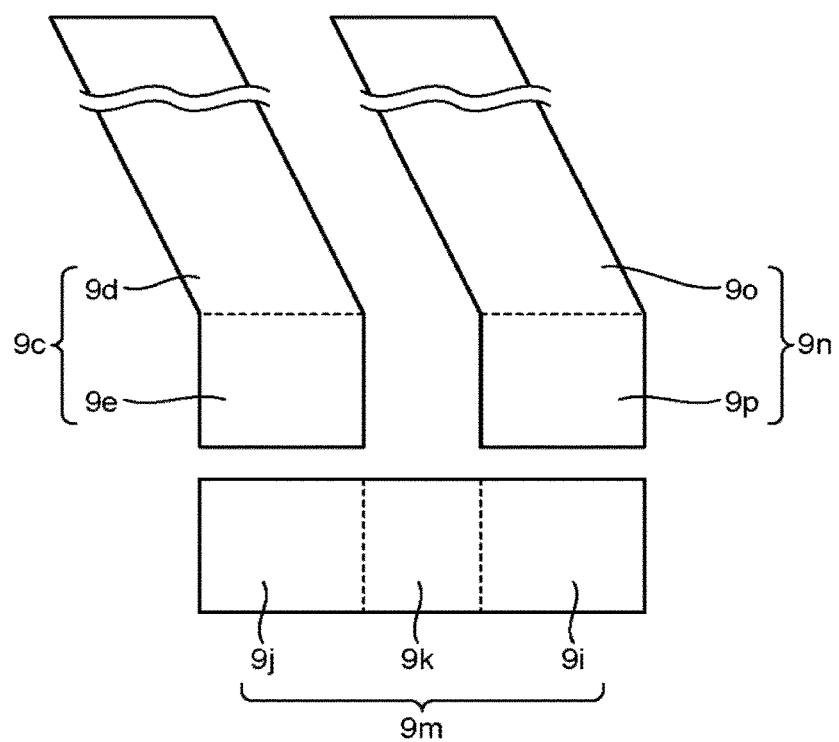
FIG. 17 is a view for explaining an example of how to attach the highly thermally conductive member according to the fifth modification.

Here, with reference to FIG. 17, an example of how to attach the highly thermally conductive member according to the fifth modification is described. FIG. 17 is a view for explaining the example of how to attach the highly thermally conductive member according to the fifth modification.

As illustrated in FIG. 17, the highly thermally conductive member according to the fifth modification is separated into three highly thermally conductive members 9c, 9n, and 9m. The highly thermally conductive members 9c and 9m according to the fifth modification are configured in the same manner as the highly thermally conductive members 9c and 9m according to the fourth modification, and description thereof is therefore omitted.

The highly thermally conductive member 9n includes the eighth highly thermally conductive member 9o and a ninth highly thermally conductive member 9p. The eighth highly thermally conductive member 9o and the ninth highly thermally conductive member 9p are integrally molded. The eighth highly thermally conductive member 9o has a substantially parallelogram-like shape when viewed from the top. The ninth highly thermally conductive member 9p is rectangular when viewed from the top.

The shape of the highly thermally conductive member 9c and the shape of the highly thermally conductive member 9n are substantially the same when viewed from the top.

Here, the example of how to attach the highly thermally conductive member according to the fifth modification is described. First, as illustrated in FIG. 16, the fifth highly thermally conductive member 9i of the highly thermally conductive member 9m is joined to the side surface 21c of the frame 21, and the sixth highly thermally conductive member 9j of the highly thermally conductive member 9m is joined to the side surface 21d of the frame 21, in the same manner as in the fourth modification. In addition, the seventh highly thermally conductive member 9k of the highly thermally conductive member 9m is joined to the back surface 21a of the frame 21.

Subsequently, as illustrated in FIG. 16, the ninth highly thermally conductive member 9p of the highly thermally conductive member 9n is stuck on the fifth highly thermally conductive member 9i. Subsequently, as illustrated in FIG. 16, the eighth highly thermally conductive member 9o of the highly thermally conductive member 9n is spirally wrapped around the cable 8.

Subsequently, as illustrated in FIG. 16, the second highly thermally conductive member 9e of the highly thermally conductive member 9c is stuck on the sixth highly thermally conductive member 9j. Subsequently, as illustrated in FIG. 14, the first highly thermally conductive member 9d of the highly thermally conductive member 9c is spirally wrapped around the cable 8.

In this manner, the highly thermally conductive members that form a double-stranded spiral are wrapped around the cable 8 in the fifth modification.

In the fourth modification described above, although the given example has a highly thermally conductive member composed separately of three highly thermally conductive members 9c, 9h, and 9m, the three highly thermally conductive members 9c, 9h, and 9m may be integrally molded. Similarly, in the fifth modification, although the given example has a highly thermally conductive member composed separately of three highly thermally conductive members 9c, 9n, and 9m, the three highly thermally conductive members 9c, 9n, and 9m may be integrally molded.

The ultrasonic probe and the ultrasonic diagnosis apparatus according to at least one of the embodiment and the modifications that are described above are capable of suppressing temperature increase of the tip part 2 during transmission and reception of ultrasonic waves.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe comprising:
a tip part including transducer elements configured to transmit and receive ultrasound waves, electronic circuitry electrically connected to the transducer elements, and a frame having the electronic circuitry provided thereon;
an operation part configured to receive operations from an operator;
a bending part including a cable electrically connected to the electronic circuitry, the bending part being configured to change an orientation of the tip part by bending in accordance with operations performed on the operation part; and
a heat conducting part including a unitary component extending from the tip part to a position which is located on an opposite side to the tip part side of the bending part with respect to an end of the tip part side of the bending part, the heat conducting part being in contact with the frame in the tip part and in the close vicinity of the cable in the bending part.

2. The ultrasonic probe according to claim 1, wherein the heat conducting part is wrapped around the cable in the bending part.

3. The ultrasonic probe according to claim 2, wherein the heat conducting part is spirally wrapped around the cable in the bending part.

4. The ultrasonic probe according to claim 1, wherein the tip part includes flexible printed circuits (FPC) serving as an intermediate for electronic connection between the electronic circuitry and the cable and provided in such a manner that the FPC do not impede thermal contact between the frame and the heat conducting part.

5. The ultrasonic probe according to claim 1, wherein
the transducer elements are located on a front surface side of the frame, and
the heat conducting part is in contact with a back surface side of the frame in the tip part.

6. The ultrasonic probe according to claim 5, wherein
the electronic circuitry is located on the front surface side of the frame, and
the tip part includes a flexible printed circuit (FPC) serving as an intermediate for electronic connection between the electronic circuitry and the cable and passing along the back surface side of the frame.

7. The ultrasonic probe according to claim 1, wherein the heat conducting part is constructed of at least one thermally conductive sheet.

8. The ultrasonic probe according to claim 7, wherein the thermally conductive sheet has thermal conductivity of at least 1 W/m·k in a thickness direction thereof and has thermal conductivity of at least 300 W/m·k in a direction along a plane perpendicular to the thickness direction.

9. The ultrasonic probe according to claim 1, wherein the electronic circuitry includes at least one of drive signal generating circuitry, delay circuitry, adder circuitry, and transmission/reception channel controlling circuitry.

10. The ultrasonic probe according to claim 1, wherein
the bending part includes angle rings configured to deform in accordance with operations on the operation part, and
the heat conducting part is located to the inner side of the angle rings in the bending part.

11. The ultrasonic probe according to claim 1, wherein
the unitary component is a sheet-like heat conducting component, and
the heat conducting part includes the heat conducting component in a folded state.

12. The ultrasonic probe according to claim 1, wherein the unitary component is constructed of a component that contains carbon graphite.

13. An ultrasonic diagnosis apparatus comprising image generation circuitry configured to generate an ultrasonic image based on output from an ultrasonic probe comprising:
a tip part including transducer elements configured to transmit and receive ultrasound waves, electronic circuitry electrically connected to the transducer elements, and a frame having the electronic circuitry provided thereon;
an operation part configured to receive operations from an operator;
a bending part including a cable electrically connected to the electronic circuitry, the bending part being configured to change an orientation of the tip part by bending in accordance with operations performed on the operation part; and a heat conducting part including a unitary component extending from the tip part to a position which is located on an opposite side to the tip part side of the bending part with respect to an end of the tip part side of the bending part, the heat conducting part being in contact with the frame in the tip part and in the close vicinity of the cable in the bending part.

14. The ultrasonic diagnosis apparatus according to claim 13, wherein the heat conducting part is wrapped around the cable in the bending part.

15. The ultrasonic diagnosis apparatus according to claim 14, wherein the heat conducting part is spirally wrapped around the cable in the bending part.

16. The ultrasonic diagnosis apparatus according to claim 13, wherein the tip part includes flexible printed circuits (FPC) serving as an intermediate for electronic connection between the electronic circuitry and the cable and provided in such a manner that the FPC do not impede thermal contact between the frame and the heat conducting part.

17. The ultrasonic diagnosis apparatus according to claim 13, wherein
the transducer elements are located on a front surface side of the frame, and
the heat conducting part is in contact with a back surface side of the frame in the tip part.

18. The ultrasonic diagnosis apparatus according to claim 13, wherein
the bending part includes angle rings configured to deform in accordance with operations on the operation part, and
the heat conducting part is located to the inner side of the angle rings in the bending part.

19. The ultrasonic diagnosis apparatus according to claim 13, wherein
the unitary component is a sheet-like heat conducting component, and
the heat conducting part includes the heat conducting component in a folded state.

* * * * *